United States Patent
Dinnequin

(10) Patent No.: US 7,199,269 B2
(45) Date of Patent: Apr. 3, 2007

(54) METHOD FOR PRODUCING STABLE SOLUTIONS OF PHENOLIC SUBSTANCES AND RESULTING SOLUTIONS

(76) Inventor: Bernard Dinnequin, Les Granges Galand, 2 allee du Petit Cher, PB 123 F-37554, Saint Avertin Cedex (FR)

( * ) Notice: Subject to any disclaimer, the term of this patent is extended or adjusted under 35 U.S.C. 154(b) by 425 days.

(21) Appl. No.: 10/495,841

(22) PCT Filed: Nov. 15, 2002

(86) PCT No.: PCT/FR02/03922

§ 371 (c)(1),
(2), (4) Date: Jul. 15, 2004

(87) PCT Pub. No.: WO03/041687

PCT Pub. Date: May 22, 2003

(65) Prior Publication Data

US 2005/0070613 A1    Mar. 31, 2005

(30) Foreign Application Priority Data

Nov. 15, 2001   (FR)   ................... 01 14796

(51) Int. Cl.
*C07C 215/00* (2006.01)
(52) U.S. Cl. .......................... 564/355; 564/374; 564/2
(58) Field of Classification Search ................ 564/355, 564/374, 2
See application file for complete search history.

(56) References Cited

U.S. PATENT DOCUMENTS 6,992,218 B2 *   1/2006   Dietlin et al. ................... 564/4

* cited by examiner

*Primary Examiner*—Samuel Barts
(74) *Attorney, Agent, or Firm*—Charles A. Muserlian

(57) ABSTRACT

A novel method for producing stabilized antioxidant-free solutions based on phenolic substances which consists in deoxygenation of the solutions with an inert gas, and in deoxygenation of gas holdups of the vessels, of the manufacturing pipes and inerting of ampoules and flasks containing the solution with a dense inert rare gas such as argon, at low temperature and with pH adjusted above 3.0 and below 5.0 to obtain stable solutions of phenolic substances containing not more than 0.02 ppm of oxygen in the solution, which is filtered by double sterilizing filtration useful for human or animal therapeutic treatment.

14 Claims, No Drawings

METHOD FOR PRODUCING STABLE SOLUTIONS OF PHENOLIC SUBSTANCES AND RESULTING SOLUTIONS

This application is a 371 of PCT/FR2002/003922 filed Nov. 15, 2002.

The invention concerns the field of therapeutic chemistry and more particularly the field of pharmaceutical technology.

It concerns specially a novel method for obtaining stable solutions of antioxidant-free and preservative-free phenolic substances.

More specifically, the aim of the invention is a manufacturing process allowing to produce stabilized solutions containing at least one phenolic substance as active ingredient whose characteristic is that these stabilized phenolic solutions are obtained by deoxygenation of phenolic substances solutions by a lighter inert gas and by deoxygenation by a dense inert gas of gas holdups of the manufacturing tanks and pipes before and after distribution of the products.

Furthermore, the process is characterized by the fact that the operations are carried out using water continuously deoxygenated by an inert gas bubbling and by the fact that the water and solution temperature is maintained preferably between 8° C. and 10° C. in order to avoid any reoxygenation with a solution pH adjusted over 3.0 and below 5.0 during its production.

The use of the process according to the invention allows to obtain solutions of phenolic substances having a dissolved oxygen content highly lower or equal to 0.02 ppm.

Under such conditions, the adding of antioxidizing agent especially the adding of sulphites, of complexing agent and/or stabilizing antiradical agent, as currently practised formerly, is no more necessary. The analysis of the solutions shows the absence of degradation product.

Moreover, this process allows to carry out the sterilization by double sterilizing filtration at room temperature or below room temperature, without having recourse to a sterilizing or tyndallizing process using heat.

Manufacturing processes are known for carrying out phenolic substances injections presenting sufficient stability criteria allowing heat sterilization of these solutions and/or their preservation for several-month periods.

In the French patent 2.740.338 (Rhône Poulenc Rorer SA) are already described new dobutamine-containing and sulphite-free formulations where the antioxidant agent is ascorbic acid or one of its derivatives used in sufficient quantity to preserve stability. According to this patent, it is nevertheless necessary to use important quantities of ascorbic acid or one of its derivatives, preferably between 3.5 and 10%. Ascorbic acid is not a harmless chemical agent and its repeated use leads to excitement states without any relationship with the recommended therapy.

Furthermore, in this document is described the used of an inert gas such as nitrogen. After heat-sterilization, the stability is not better.

In the European patent 187.019 (Eli Lilly) are described dobutamine salts preparations taking care to add into the reactive medium a hydroxyle collector under nitrogen atmosphere. No information is given concerning the solution stability and the method of sterilization.

The international patent WO94/13274 (Abbott) describes pharmaceutical formulations containing a catecholamine and a metallic ions-chelating agent with a pH adjustment leading to frankly acid values going from 1.5 to about 4.0. The solutions stability is ensured by such factors. Moreover, the gas holdup is measured and the oxygen content is adjusted by a nitrogen stream. Nothing is indicated concerning the oxygen influence on the stability of these solutions.

The international patent WO98/05314 (Pharmatop) describes formulations containing paracetamol dissolved in an aqueous solvent where are added a buffer (pH 4 to 8) and a free-radicals collector, taking care to make bubble in the aqueous solvent an inert gas insoluble in water preferably nitrogen. It is observed that the quantity of secondary compounds perceptibly rises after autoclaving but that nitrogen bubbling reduces clearly the appearance of a pink colouring into the sterilized solutions heated at 120° C.

The former tests have therefore been performed after adding of an antioxidant agent or of an antiradical agent into the phenolic substance solutions in order to avoid any oxidation of the molecules. Furthermore, the nitrogen bubbling into the solutions contributes to their stability and allows to heat the solutions at 120° C. and more. It keeps the solutions in a state where they remain colourless. The documents of the former know-how specify that the adding of an antioxidant or a complexing agent constitutes the key-element to protect the molecules from oxidation. According to these documents, the use of vacuum could also be a favourable factor.

It can therefore be considered that the former processes used to carry out phenolic substances solutions had recourse to complicated techniques using necessarily one ore several antioxidant agents and using overall a heat-sterilizing process which increases the risk of molecules deterioration. Actually, the phenolic molecules oxidation occurs even with very small amounts of oxygen present in the medium and metallic traces presence contributes to accelerate the oxidation process during the heating phase for sterilization.

According to the invention, the process presents the advantage of avoiding any requirement to the use of antioxidant agent, of complexing agent, of preservative agent, or buffer solution and to allow a low temperature sterilization. By this way, the molecules oxidation risks are considerably restricted. It is understood that the so-called easily oxidizable substances may be particularly catecholamines derivatives i.e aromatic compounds possibly substituted on the aromatic cycle by one or several hydroxyl groups and bearing and α-hydroxylated or ketonic aliphatic chain and a terminal substituted or not, amine group. As catecholamines examples, it may be quoted adrenaline, noradrenaline, isosuproxine, isoprenaline, dobutamine, dopamine, dimetofrine dipivefrine, ephedrine, ibopamine, metaraminol, octopamine, phenylpropanolamine, phenylpropymethylamine, pholedrine, propylhexedrine, pseudoephedrine, adrenalone, amidephrine, metaproterenol, paracetamol or propacetamol.

These molecules undergo easily an oxidation giving birth to strongly coloured quinonic structures attesting then the active principle decomposition.

Are added problems linked to the instability of the active principle. Catecholamines injections are stable under some conditions provided sulphites are added as antioxidant but 3 reaction processes contributing to the molecule degradation are involved:

A racemization phenomenon: racemization of adrenaline or noradrenaline solutions mainly linked to pH or temperature for example is a known phenomenon. It leads to the development of a dextrogyre isomer having few pharmacological activity. The reaction of racemization may be important at a pH less than 3.0. It is accelerated by temperature increasing. It is reduced when the solution is maintained at low temperature.

A chemical and photochemical oxidation phenomenon leading to coloured degradation products, though the absence of appearance of colour is not able to guarantee the preservation of active principles. The colouring phenomenon is accelerated by heat. The presence of metallic traces is capable of exerting some influence on oxidation phenomenons. Sulphites limit considerably this oxidation and prevent from coloured derivatives forming.

A reaction of addition with sulphites: the protective effect is mainly linked to a chemical reaction of addition on catecholamines leading to the forming of [1-(3,4-dihydrophenyl)2-aminoethane] (or propane) sulphonic acid. It is the specific case for adrenaline or noradrenaline. This reaction of addition is accelerated by heating.

The technical problem to be solved consisted therefore to avoid using sulphites by reason of their allergizing properties and to stop the use of any antioxidant agent and simultaneously to avoid heat sterilization when injections are going to be realized.

This problem has been solved by protecting efficiently from oxygen the phenolic substances solutions by use of water for injections being deoxygenated by nitrogen bubbling and by inerting of residual volumes, of manufacturing tanks, of pipes and of manufacturing containers by a dense inert gas such as freons, argon, xenon, (36)-kripton or neon, determining the residual oxygen concentration by oxymetry and other gases, by gas chromatography, maintaining the temperature below 25° C. to avoid reoxygenation (preferably from 0° C. to 20° C.) and overall at about 20° C. and carrying out the preparation under aseptic conditions, under thorough inerting with -the aid of inert above-mentioned gases, and finally filling as well the containers with the aid of the above-mentioned gases.

Under these conditions, the assays indicate that if water for injections contains about 0.1 ppm of dissolved oxygen, the oxygen content of the solution before filtration and the residual oxygen content into the primary packaging are often widely lower than 2 ppm.

The use of these protective measures has allowed the manufacture of injections being stable for at least a 12-month storage period. A stability at least equal to that of the sulphites-containing solutions is obtained without the disadvantages linked to these products and without risk of sulphonation products forming.

According to a special operating procedure of the invention the manufacturing process of stable phenolic substances solutions presents the following stages:

1. Dissolution of the active principle and of the possible excipients such as sodium chloride, in water for sterile preparations previously degased by nitrogen bubbling until a residual dissolved oxygen content lower or equal to 0.02 ppm in manufacturing tanks where the residual volumes are oxygen-free by introduction of a dense inert gas such as argon, xenon, freons . . .
2. Nitrogen bubbling into the solution during dissolution and covering the dissolution tank with an argon layer.
3. Adjustment of pH and checking the homogeneity of the solution avoiding any bacterial contamination.
4. 1 st sterilizing filtration process by pushing the solution with the aid of the inert gas, through the sterilizing filter, maintaining into the collecting tank, a covering layer of a dense gas such as argon.
5. 2nd sterilizing filtration process the covering of the solution ensuring by an argon layer of the surface to be distributed under a slight overpressure of the surface and containers and then distribution and possible plugging of the containers previously filled with inert gas.

Nitrogen bubbling and the presence of a dense inert gas such as argon take place along the manufacturing stages. By this way, the oxygen limit content in the finished product is clearly lower than 2 ppm.

Nitrogen or any other inert gas is used to degas water for injections, the solution during the manufacturing process and during the double sterilizing filtration, when transferring the solution into the transfer tank and to degas the solution when filling the ampoules. When speaking about "nitrogen" it is understood that it is the pure gas or any inert gaseous mixture where nitrogen is present.

Argon or any other dense inert gas is used for deoxygenation of the manufacturing tanks and for their covering (manufacturing and transfer tanks) as well as for deoxygenation of empty ampoules or vials and for inerting the residual volume of filled ampoules and vials. When speaking about "argon" it is understood that it means any gas or gaseous mixture containing only argon or argon mixed with a different noble gas denser than air.

The solutions inerting in vials or ampoules is necessary and prevents the catecholamine salt from oxidation leading to the appearance of degradation products which are searched when controlling the finished product.

In order to validate the inerting operation with nitrogen and argon or with any other inerting inert gas as abovementioned, dissolved residual oxygen measurements in the solution have been carried out and specifications have been fixed.

These in-process controls are carried out during each run at the following stages:

1. Residual oxygen control in water for injections
   Specification: $\leq 0.02$ ppm of oxygen
2. Residual oxygen control in the solution before filtration
   Specification: $\leq 0.02$ ppm of oxygen
3. Residual oxygen control in the container by measurement of argon, nitrogen and residual oxygen
   Argon in the container head space: $\leq 70\%$
   Nitrogen: $\leq 30\%$
   Oxygen: $\leq 4\%$ The gas chromatographic analysis of inerting gases used in these operations, shows a full purity of the gas and a practically total absence of oxygen.

The use of argon or other inert gases, needs to carry out tests in order to fix the optimal conditions of use, particularly for the containers inerting which constitutes the most important critical point. These tests have been carried out as part of pharmaceutical development without preservatives nor antioxidant, of catecholamine-based solutions (noradrenaline, adrenaline, dopamine, dobutamine etc . . . )

preservative-free noradrenaline solution 0.2% (8 mg/4 ml and 16 mg/8 ml)

preservative-free noradrenaline solution at 0.025% and 0.1% packaged in 1 ml, 5 ml and 10 ml ampoules preservative-free dopamine hydrochloride solution 50 mg and 200 mg per 5 ml.

dobutamine hydrochloride solution at 2.5% (w/v)—250 mg preservative-free in 20 ml vials etc . . .

The aim of these tests were the determination of:
the inert gases optimal pressures to apply to the inerting points of the ampoules filling machine
the speed of the distributing-sealing line considering the obtained quality of inerting.

The basic parameters (speed of the line and argon pressure) have been fixed at starting considering the obtained results.

The tests have been carried out during the distribution of 60 l of w.f.i. adjusted at pH 3.1, prepared according to the protocol above-described (residual oxygen content ≦0.01 ppm) and distributed in 5 ml ampoules.

Description of Tests

Test N° 1

A study of the influence of argon pressure and of the distribution speed on dissolved $O_2$ content in the finished products was carried out. Each parameter is independently altered in order to determine the optimal value.
1. argon pressure variation form 35 mPa/h to 75 mPa/h (3.5 to 7.5 bars) with a standard speed of 7500 vials/hour
2. distribution speed variation from 5000 to 10000 vials/hour with a fixed argon pressure.

Test N° 2

Study of homogeneity in time keeping both optimal parameters, then study of the influence of prolonged stops (5 and 10 minutes) of the packaging line.
1. measurement of $O_2$ content every 5 minutes for 30 minutes
2. measurement of $O_2$ content after two prolonged stops of 5 and 10 minutes with a follow-up every minute from the rerun.

Results

1. Influence of Argon Pressure at Filling Machine Level
Altered parameters: argon pressure variation (from 3500 to 7500 mPa/h) with a fixed speed of 7500 products/hour
2. Influence of the Distribution Machine Speed
Altered parameters: variation of the speed of the distributing machine from 5760 to 9000 products/hour. The selected argon pressure is constant in order to check whether it is possible to find results equivalent to those obtained in the former test.

The more the distribution line speed is increasing, the more the oxygen content in the ampoules is increasing: average: 0.62 ppm.

In case of stopping for products placed in the filling station the dissolved oxygen contents are clearly higher (from 0.75 to 1.87 ppm). For the products going to receive gas when stopping, the values are complying with specification. For the products having just received gas when stopping, the contents are weaker than the normal content according to the stop duration. This demonstrates the efficacy of the covering by an inert gas such as argon.

3. Conclusion

Argon pressure in the filling machine must be fixed according to the distributing machine speed at 7200 products/hour.

Special Conditions to be Respected
  The collecting tank must be immediately placed under argon after filtration and maintained under argon pressure for the full duration of filling.
  A the beginning of filling, the line must be carefully cleared.
  In case of stopping of the machine, it is necessary to do away with the unplugged filled products or with the empty products having previously received gas.

Another important factor of degradation is light exposure. The experiment showed the need to operate protected from light. Tests carried out at 25° C. under light showed the presence of a coloured precipitate from the 5th day and an impurities concentration higher than 3% including especially adenochrome. Operating at 30° C. and over, the results are more quickly non complying and out of quality specification.

CONCLUSION

The catecholamines solution without preservative can be perfectly stored for 12 months at 2° C./8° C. The solution remains clear and colourless. The pH does not vary.

No impurity is appearing and the assay result complies with specification.

At 25° C. under light (light and 60 p. cent of relative humidity) the solution becomes slightly coloured after a 6-month storage, impurities are appearing but remain under the fixed limits.

The pH does not vary.

The active principle concentration decreases and becomes out of specification after 9 months of storage.

The invention concerns as well catecholamines-based injections to the best they are prepared according to the invention process. They are especially employed for human or animal therapeutic treatment as hypertensive agents and/or analgesics.

The following examples are useful to clarify the invention without however any limit of it.

EXAMPLE 1

| Noradrenaline 0.2% (w/v) injection i.e. 8 mg/4 ml. Formula for one industrial batch | |
| --- | --- |
| Noradrenaline | 400.0 g |
| pH = 3 to 5 | |
| Water for injections to make | 200.0 litres |
| Nitrogen | appropriate quantity |
| Argon | appropriate quantity |

EXAMPLE 2

| Dopamine | 10 kg |
| --- | --- |
| pH = 3 to 5 | |
| Water for injections | to make 250.0 litres |
| Nitrogen | appropriate quantity |
| Argon | appropriate quantity |

EXAMPLE 3

| Dopamine | 2.5 kg |
| --- | --- |
| pH = 3 to 5 | |
| Water for injections | to make 250.0 litres |
| Nitrogen | appropriate quantity |
| Argon | appropriate quantity |

The manufacturing processes and the controls are as follows.

Stage 0

Water for injections is cooled and the dissolved oxygen content is stabilized at a maximum of 0.02 ppm by nitrogen or another inert gas bubbling.

Stage 1

The manufacturing tank is deoxygenated by covering by a layer of argon or by another dense inert gas.

The active principle and the excipients are dissolved under nitrogen or another inert gas bubbling and the pH is adjusted between 3 and 5. The dissolved oxygen content is stabilized at a maximum of 0.02 ppm.

Stage 2

The solution undergoes a double sterilizing filtration under an argon or another dense inert gas atmosphere.

Stage 3

The solution is distributed under a double inerting: a pre-inerting by nitrogen or by any other inert gas and a post-inerting by nitrogen or by any other dense inert gas in order to ensure a perfectly defined content of dissolved oxygen in the solution and of residual oxygen in the residual volume of the packaging.

The obtained results are as follows:

EXAMPLE 1

Noradrenaline Solutions a) Dissolved Oxygen

The dissolved oxygen content is perfectly controlled along the manufacturing steps; for that, regular measurements at different stages are carried out. The obtained results along the process on 2 batches are given in the following table:

| Batches | Specification | Dissolved oxygen (ppm) | | | | |
|---|---|---|---|---|---|---|
| | | Water for injections | Tank after excipients dissolution | Tank after active principle dissolution | Tank after pH adjustment | Tank before filtration |
| A | ≦0.02 ppm | 0.02 | 0.02 | 0.02 | 0.02 | 0.02 |
| B | ≦0.02 ppm | 0.02 | 0.02 | 0.01 | 0.01 | 0.01 |

The obtained results for dissolved oxygen in the finished products are hereafter reported.

| Batches | Specification | Results |
|---|---|---|
| A | ≦3 ppm | 0.98 |
| B | ≦3 ppm | 0.83 |

They are hereafter detailed from 25 tests per batch.

| | Batch n° | | | | | | | | | | |
|---|---|---|---|---|---|---|---|---|---|---|---|
| | A | | | | | B | | | | | |
| Samples | 1 | 2 | 3 | 4 | 5 | 1 | 2 | 3 | 4 | 5 | 1 |
| Beginning of batch | 0.81 | 1.09 | 1.04 | 0.87 | 0.92 | 0.72 | 1.08 | 0.92 | 0.68 | 0.96 | 0.94 |
| Quarter of batch | 1.02 | 1.13 | 0.75 | 0.98 | 0.74 | 1.00 | 1.15 | 0.64 | 0.64 | 0.66 | 0.94 |
| Middle of batch | 0.89 | 0.85 | 0.94 | 0.98 | 1.15 | 0.66 | 1.00 | 0.91 | 0.83 | 0.64 | 0.91 |
| ¾ of batch | 1.02 | 0.89 | 1.17 | 1.17 | 1.06 | 0.89 | 0.68 | 0.96 | 1.00 | 0.72 | 0.94 |
| End of batch | 1.28 | 0.98 | 0.94 | 1.21 | 0.72 | 0.64 | 0.85 | 1.04 | 0.91 | 0.64 | 0.70 |
| Mean | | | 0.98 | | | | | 0.83 | | | |
| Standard deviation | | | 0.152 | | | | | 0.165 | | | |
| Relative standard deviation (p. cent) | | | 15.48 | | | | | 19.89 | | | |
| Mini | | | 0.72 | | | | | 0.64 | | | |
| Maxi | | | 1.28 | | | | | 1.15 | | | | b) Assay of Residual Argon, Nitrogen and Oxygen

The results of assays by gas chromatography for argon, nitrogen and oxygen carried out in the headspace after filling are hereafter detailed.

| | Argon content (p. cent v/v) | Nitrogen content (p. cent v/v) | Oxygen content (p. cent v/v) |
|---|---|---|---|
| | Batch A | | |
| Beginning of batch | 85.8 | 14.0 | 3.0 |
| Middle of batch | 86.1 | 10.6 | 1.8 |
| End of batch | 89.0 | 9.7 | 1.6 |
| | Batch B | | |
| Beginning of batch | 85.4 | 11.0 | 1.8 |
| Middle of batch | 86.7 | 10.6 | 1.7 |
| End of batch | 86.9 | 11.9 | 1.8 |

The results of assays of residual argon, oxygen and nitrogen on 5 samples of finished products per batch are hereafter mentioned.

| | Argon content (p. cent v/v) | Nitrogen content (p. cent v/v) | Oxygen content (p. cent v/v) |
|---|---|---|---|
| | Batch A | | |
| 1 | 85.8 | 14.0 | 3.0 |
| 2 | 82.1 | 12.2 | 2.5 |
| 3 | 81.3 | 8.9 | 0 |

-continued

|   | Argon content (p. cent v/v) | Nitrogen content (p. cent v/v) | Oxygen content (p. cent v/v) |
|---|---|---|---|
| 4 | 86.1 | 10.6 | 1.8 |
| 5 | 89.0 | 9.7 | 1.6 |
| Mean | 84.86 | 11.08 | 1.78 |
| Standard deviation | 3.156 | 2.041 | 1.141 |
| Relative standard deviation (p. cent) | 3.72 | 18.42 | 64.10 |
| Batch B | | | |
| 1 | 86.1 | 11.05 | 1.8 |
| 2 | 85.4 | 4.7 | 0.1 |
| 3 | 82.1 | 9.7 | 1.6 |
| 4 | 86.7 | 10.6 | 1.7 |
| 5 | 86.9 | 11.9 | 1.8 |
| Mean | 85.44 | 9.59 | 1.40 |
| Standard deviation | 1.956 | 2.846 | 0.731 |
| Relative standard deviation (p. cent) | 2.29 | 29.68 | 52.24 | c) In-process Controls

|   | Controls | Specification | Batch A | Batch B |
|---|---|---|---|---|
| Water for injections | Temperature | 8° C./10° C. | 10° C. | 9° C. |
| | Conductivity | $\leq 1\ \mu S \cdot cm^{-1}$ | 0.66 | 0.40 |
| | Dissolved $O_2$ | $\leq 0.02$ ppm | 0.02 ppm | 0.02 ppm |
| | L.A.L test | <0.25 IU/ml | <0.25 IU/ml | <0.25 IU/ml |
| Control of the solution | clarity and opalescence | $\leq$Standard I $\leq$Standard R7 and YB7 | $\leq$Standard I $\leq$Standard R7 and YB7 | $\leq$Standard I $\leq$Standard R7 and YB7 |
| | density | close to 1.0060 | 1.0066 | 1.0065 |
| | microbial contamination of the solution before filtration | $\leq 10$ CFU/ml | 0.1 | 10 |
| | microbial contamination between both filtrations | $\leq 10$ CFU/100 ml | 0 | 0 |
| Filling | Distribution volume | $\geq 4.0$ ml | 4.18 ml | 14.17 ml |
| | Dissolved $O_2$ | $\leq 3$ ppm | 0.98 ppm | 0.83 ppm | d) Finished Product Controls

The controls have been carried out on 5 samples per batch taken along the manufacturing process.

| Nature of controls | Specification | Beginning | ¼ | Middle | ¾ | End |
|---|---|---|---|---|---|---|
| | | Batch A | | | | |
| Appearance | | | | | | |
| Clarity | Clear | Clear | Clear | Clear | Clear | Clear |
| Colour | $\leq$YB7 | YB7 | YB7 | YB7 | YB7 | YB7 |
| Related substances and degradation products | | | | | | |
| a) | $\leq 1.0$ ppm | ND | ND | ND | ND | ND |
| b) | $\leq 0.1$ ppm | ND | ND | ND | ND | ND |
| c) | $\leq 1.0$ ppm | ND | ND | ND | ND | ND |
| d) | $\leq 1.0$ ppm | ND | ND | ND | ND | ND |
| e) | $\leq 0.1$ ppm | ND | ND | ND | ND | ND |
| sum of substances | $\leq 3.0$ ppm | ND | ND | ND | ND | ND |
| Assay | 7.60 to 8.40 mg | 8.36 | 8.33 | 8.44 | 8.36 | 8.36 |
| | | Batch B | | | | |
| Appearance | | | | | | |
| Clarity | Clear | Clear | Clear | Clear | Clear | Clear |
| Colour | $\leq$YB7 | YB7 | YB7 | YB7 | YB7 | YB7 |
| Related substances and degradation products | | | | | | |
| a) | $\leq 1.0$ ppm | ND | ND | ND | ND | ND |
| b) | $\leq 0.1$ ppm | ND | ND | ND | ND | ND |
| c) | $\leq 1.0$ ppm | ND | ND | ND | ND | ND |

-continued

| Nature of controls | Specification | Beginning | ¼ | Middle | ¾ | End |
|---|---|---|---|---|---|---|
| d) | ≦1.0 ppm | ND | ND | ND | ND | ND |
| e) | ≦0.1 ppm | ND | ND | ND | ND | ND |
| sum of substances | ≦3.0 ppm | ND | ND | ND | ND | ND |
| Assay | 7.60 to 8.40 mg | 8.31 | 8.36 | 8.37 | 8.35 | 8.36 |

ND = not detected

EXAMPLE 2

Dopamine Solution 1% a) Dissolved Oxygen

The dissolved oxygen rate is perfectly controlled along the manufacturing stages; for that, measurements are regularly carried out at various stages.

The obtained in-process results on 3 batches are reported on the table below:

|  |  | Dissolved oxygen (ppm) | | | |
|---|---|---|---|---|---|
| Batches | Specification | Water for injections | Tank after dissolution | Tank after pH adjustment | Tank before filtration |
| C | ≦0.02 ppm | 0.01 | 0.02 | 0.01 | 0.01 |
| D | ≦0.02 ppm | 0.01 | 0.02 | 0.01 | 0.01 |
| E | ≦0.02 ppm | 0.01 | 0.02 | 0.01 | 0.01 |

The dissolved oxygen obtained results in the finished products are reported hereunder.

| Batches | Specification | Results |
|---|---|---|
| C | ≦3 ppm | 0.59 |
| D | ≦3 ppm | 0.56 |
| E | ≦3 ppm | 0.57 |

They are hereafter detailed from 12 tests per batch.

b) Assay of Residual Argon, Nitrogen and Oxygen

The results of assays by gas chromatography of argon, nitrogen and oxygen carried out in the headspace after filling are hereafter detailed.

|  | Argon content (p. cent v/v) | Nitrogen content (p. cent v/v) | Oxygen content (p. cent v/v) |
|---|---|---|---|
|  | Batch C | | |
| Beginning of batch | 87.9 | 11.0 | 1.3 |
| Middle of batch | 88.0 | 11.3 | 0.2 |
| End of batch | 88.1 | 11.0 | 0.2 |
|  | Batch D | | |
| Beginning of batch | 90.8 | 8.4 | 0.7 |
| Middle of batch | 91.1 | 9.6 | 0.1 |
| End of batch | 92.7 | 8.9 | 0.1 |
|  | Batch E | | |
| Beginning of batch | 91.5 | 8.8 | 0.7 |
| Middle of batch | 92.8 | 9.2 | 0.2 |
| End of batch | 92.3 | 9.1 | 0.2 |

The assay results of residual argon, oxygen and nitrogen on 5 samples of finished products per batch are hereafter mentioned.

|  | Argon content (p. cent v/v) | Nitrogen content (p. cent v/v) | Oxygen content (p. cent v/v) |
|---|---|---|---|
|  | Batch C | | |
| 1 | 87.9 | 11.0 | 1.3 |
| 2 | 94.5 | 4.7 | 0.2 |
| 3 | 92.9 | 9.2 | 0.2 |

|  | Batches n° | | | | | | | | | | |
|---|---|---|---|---|---|---|---|---|---|---|---|
|  | C | | | | D | | | | E | | | |
| Samples | 1 | 2 | 3 | 4 | 1 | 2 | 3 | 4 | 1 | 2 | 3 | 4 |
| Beginning of batch | 0.70 | 0.66 | 0.45 | 0.58 | 0.60 | 0.58 | 0.43 | 0.62 | 0.60 | 0.57 | 0.45 | 0.58 |
| Middle of batch | 0.62 | 0.62 | 0.49 | 0.60 | 0.60 | 0.62 | 0.45 | 0.58 | 0.64 | 0.64 | 0.49 | 0.60 |
| End of batch | 0.60 | 0.60 | 0.53 | 0.57 | 0.60 | 0.60 | 0.47 | 0.57 | 0.60 | 0.60 | 0.47 | 0.60 |
| Mean | 0.59 | | | | 0.56 | | | | 0.57 | | | |
| Standard deviation | 0.0689 | | | | 0.0686 | | | | 0.0645 | | | |
| Relative standard deviation (p. cent) | 11.76 | | | | 12.20 | | | | 11.27 | | | |
| Mini | 0.45 | | | | 0.43 | | | | 0.45 | | | |
| Maxi | 0.70 | | | | 0.62 | | | | 0.64 | | | |

-continued

|   | Argon content (p. cent v/v) | Nitrogen content (p. cent v/v) | Oxygen content (p. cent v/v) |
|---|---|---|---|
| 4 | 88.0 | 11.3 | 0.2 |
| 5 | 88.1 | 11.0 | 0.1 |
| Mean | 90.28 | 9.44 | 0.4 |
| Standard deviation | 3.17 | 2.78 | 0.50 |
| Relative standard deviation (p. cent) | 3.52 | 29.41 | 126.24 |
| Batch D | | | |
| 1 | 90.8 | 8.4 | 0.7 |
| 2 | 91.1 | 9.6 | 0.1 |
| 3 | 92.7 | 8.9 | 0.1 |
| 4 | 93.1 | 8.7 | 0.0 |
| 5 | 88.6 | 9.9 | 0.1 |
| Mean | 91.26 | 9.1 | 0.2 |
| Standard deviation | 1.79 | 0.63 | 0.28 |
| Relative standard deviation (p. cent) | 1.96 | 6.91 | 141.4 |

-continued

|   | Argon content (p. cent v/v) | Nitrogen content (p. cent v/v) | Oxygen content (p. cent v/v) |
|---|---|---|---|
| Batch E | | | |
| 1 | 91.5 | 8.8 | 0.7 |
| 2 | 96.4 | 4.2 | 0.2 |
| 3 | 96.9 | 4.1 | 0.1 |
| 4 | 92.8 | 9.2 | 0.2 |
| 5 | 92.3 | 9.1 | 0.0 |
| Mean | 93.98 | 7.08 | 0.24 |
| Standard deviation | 2.49 | 2.68 | 0.27 |
| Relative standard deviation (p. cent) | 2.65 | 37.84 | 112.58 | c) In-process Controls

|   | Controls | Specification | Batch C | Batch D | Batch E |
|---|---|---|---|---|---|
| Water for injections | Temperature | 8° C./10° C. | 10° C. | 9° C. | 9° C. |
|   | Conductivity | $\leq 1\ \mu S \cdot cm^{-1}$ | 0.47 | 0.47 | 0.47 |
|   | Dissolved $O_2$ | $\leq 0.02$ ppm | 0.01 ppm | 0.01 ppm | 0.01 ppm |
|   | L.A.L test | <0.25 IU/ml | <0.25 IU/ml | <0.25 IU/ml | <0.25 IU/ml |
|   | Microbial contamination | | | | |
|   | Bacteria | $\leq 10$ CFU/100 ml | 2 | 2 | 2 |
|   | Funghi | $\leq 10$ CFU/100 ml | 0 | 0 | 0 |
| Control of the solution | clarity and opalescence | $\leq$Standard I $\leq$Standard R7 and YB7 | $\leq$Standard I $\leq$Standard R7 and YB7 | $\leq$Standard I $\leq$Standard R7 and YB7 | $\leq$Standard I $\leq$Standard R7 and YB7 |
|   | density | close to 1.0110 | 1.0114 | 1.0114 | 1.0114 |
|   | microbial contamination of the solution before filtration | $\leq 10$ CFU/ml | <10 | <10 | <10 |
|   | microbial contamination between both filtrations | $\leq 10$ CFU/100 ml | 0 | 0 | 0 |
| Filling | Distribution volume | $\geq 5.0$ ml | 5.20 ml | 5.20 ml | 5.20 ml |
|   | Dissolved $O_2$ | $\leq 3$ ppm | 0.59 ppm | 0.56 ppm | 0.57 ppm | d) Controls on Finished Product

The controls have been carried out on 5 samples per batch taken all along the manufacturing process.

| Nature of controls | Specification | Beginning | ¼ | Middle | ¾ | End |
|---|---|---|---|---|---|---|
| Batch C | | | | | | |
| Appearance | | | | | | |
| Clarity | Clear | Clear | Clear | Clear | Clear | Clear |
| Colour | $\leq$YB7 | YB7 | YB7 | YB7 | YB7 | YB7 |
| Impurities | | | | | | |
| 1) | $\leq 0.05$ p. cent | <0.0005 | <0.0005 | <0.0005 | <0.0005 | <0.0005 |
| 2) | $\leq 0.05$ p. cent | <0.0005 | <0.0005 | <0.0005 | <0.0005 | <0.0005 |
| Assay | 190.0 to 210.0 mg. | 201.4 | 200.6 | 201.3 | 201.7 | 201.2 |
| Batch D | | | | | | |
| Appearance | | | | | | |
| Clarity | Clear | Clear | Clear | Clear | Clear | Clear |
| Colour | $\leq$YB7 | YB7 | YB7 | YB7 | YB7 | YB7 |

-continued

| Nature of controls | Specification | Beginning | ¼ | Middle | ¾ | End |
|---|---|---|---|---|---|---|
| Impurities | | | | | | |
| 1) | ≦0.05 p. cent | <0.0005 | <0.0005 | <0.0005 | <0.0005 | <0.0005 |
| 2) | ≦0.05 p. cent | <0.0005 | <0.0005 | <0.0005 | <0.0005 | <0.0005 |
| Assay | 190.0 to 210.0 mg | 200.7 | 200.6 | 201.0 | 201.5 | 201.8 |

Batch E

| | | | | | | |
|---|---|---|---|---|---|---|
| Appearance | | | | | | |
| Clarity | Clear | Clear | Clear | Clear | Clear | Clear |
| Colour | ≦YB7 | YB7 | YB7 | YB7 | YB7 | YB7 |
| Impurities | | | | | | |
| 1) | ≦0.05 p. cent | <0.0005 | <0.0005 | <0.0005 | <0.0005 | <0.0005 |
| 2) | ≦0.05 p. cent | <0.0005 | <0.0005 | <0.0005 | <0.0005 | <0.0005 |
| Assay | 190.0 to 210.0 mg | 202.2 | 201.7 | 202.4 | 201.5 | 201.5 |

EXAMPLE 3

Isoprenaline Hydrochloride Injection a) Dissolved Oxygen

The dissolved oxygen rate is perfectly controlled all along the manufacturing stages; for that, measurements are regularly carried out at various stages.

The obtained in-process results on 3 batches are reported on the table below:

| Batches | Specification | Water for injections | Tank after dissolution of the active principle | Tank after pH adjustment | Tank before filtration |
|---|---|---|---|---|---|
| | | Dissolved oxygen (ppm) | | | |
| F | ≦0.02 ppm | 0.02 | 0.00 | 0.00 | 0.00 |
| G | ≦0.02 ppm | 0.02 | 0.00 | 0.00 | 0.00 |
| H | ≦0.02 ppm | 0.02 | 0.00 | 0.00 | 0.00 |

The dissolved oxygen results in the finished products are hereunder reported.

| Batches | Specification | Results |
|---|---|---|
| F | ≦3 ppm | 1.13 |
| G | ≦3 ppm | 1.16 |
| H | ≦3 ppm | 0.85 |

They are hereafter detailed from 12 tests per batch.

| | Batches n° | | | | | | | | | | | |
|---|---|---|---|---|---|---|---|---|---|---|---|---|
| | F | | | | G | | | | H | | | |
| Samples | 1 | 2 | 3 | 4 | 1 | 2 | 3 | 4 | 1 | 2 | 3 | 4 |
| Beginning of batch | 1.09 | 1.02 | 0.96 | 1.19 | 1.32 | 1.25 | 1.21 | 1.15 | 1.21 | 0.83 | 0.9 | 0.81 |
| Middle of batch | 0.99 | 1.10 | 1.22 | 1.21 | 0.99 | 1.17 | 1.28 | 0.99 | 1.05 | 0.81 | 0.85 | 0.73 |
| End of batch | 1.26 | 1.26 | 1.19 | 0.99 | 1.28 | 0.98 | 1.21 | 1.09 | 0.96 | 0.66 | 0.77 | 0.66 |
| Mean | 1.134 | | | | 1.162 | | | | 0.853 | | | |
| Standard deviation | 0.111 | | | | 0.119 | | | | 0.159 | | | |
| Relative standard deviation (p. cent) | 9.79 | | | | 10.24 | | | | 18.64 | | | |
| Mini | 0.99 | | | | 0.98 | | | | 0.66 | | | |
| Maxi | 1.26 | | | | 1.28 | | | | 1.21 | | | | b) Assay of Residual Argon, Nitrogen and Oxygen

The results of assays by gas chromatography of argon, nitrogen and oxygen carried out in the headspace after filling are hereafter detailed.

| | Argon content (p. cent v/v) | Nitrogen content (p. cent v/v) | Oxygen content (p. cent v/v) |
|---|---|---|---|
| | Batch F | | |
| Beginning of batch | 74.4 | 22.1 | 1.5 |
| Middle of batch | 72.5 | 24.6 | 0.4 |
| End of batch | 71.6 | 26.7 | 0.4 |

|  | Argon content (p. cent v/v) | Nitrogen content (p. cent v/v) | Oxygen content (p. cent v/v) |
| --- | --- | --- | --- |
| Batch G | | | |
| Beginning of batch | 72.3 | 21.8 | 3.8 |
| Middle of batch | 80.3 | 19.4 | 0.4 |
| End of batch | 77.3 | 22.4 | 0.4 |
| Batch H | | | |
| Beginning of batch | 83.1 | 17.3 | 1.2 |
| Middle of batch | 82.6 | 18.1 | 0.4 |
| End of batch | 80.3 | 20.0 | 0.1 |

The assay results of residual argon, oxygen and nitrogen on 5 samples of finished products per batch are hereafter mentioned.

|  | Argon content (p. cent v/v) | Nitrogen content (p. cent v/v) | Oxygen content (p. cent v/v) |
| --- | --- | --- | --- |
| Batch F | | | |
| 1 | 69.8 | 24.0 | 3.8 |
| 2 | 74.4 | 22.1 | 1.5 |
| 3 | 72.5 | 24.6 | 0.4 |
| 4 | 71.6 | 26.7 | 0.5 |
| 5 | 67.5 | 29.0 | 0.2 |
| Mean | 71.04 | 25.28 | 1.28 |
| Standard deviation | 2.62 | 2.65 | 1.50 |
| Relative standard deviation (p. cent) | 3.69 | 10.47 | 116.4 |
| Batch G | | | |
| 1 | 72.3 | 21.8 | 3.8 |
| 2 | 71.4 | 25.2 | 1.3 |
| 3 | 80.3 | 19.4 | 0.4 |
| 4 | 97.3 | 22.4 | 0.4 |
| 5 | 72.1 | 27.4 | 0.1 |
| Mean | 74.68 | 23.24 | 1.2 |
| Standard deviation | 3.92 | 3.11 | 1.52 |
| Relative standard deviation (p. cent) | 5.25 | 13.38 | 126.8 |
| Batch H | | | |
| 1 | 78.5 | 18.0 | 0.7 |
| 2 | 83.1 | 17.3 | 0.2 |
| 3 | 82.6 | 18.1 | 0.4 |
| 4 | 80.3 | 20.0 | 0.1 |
| 5 | 78.4 | 21.3 | 0.2 |
| Mean | 80.58 | 18.94 | 0.98 |
| Standard deviation | 2.21 | 1.66 | 1.21 |
| Relative standard deviation (p. cent) | 2.74 | 8.74 | 123.4 | c) In-process Controls

| | Controls | Specification | Batch F | Batch G | Batch H |
| --- | --- | --- | --- | --- | --- |
| Water for injections | Temperature | 8° C./10° C. | 9° C. | 9° C. | 9° C. |
| | Conductivity | ≦1 µS · cm−1 | 0.47 | 0.47 | 0.47 |
| | Dissolved O₂ | ≦0.02 ppm | 0.02 ppm | 0.02 ppm | 0.02 ppm |
| | L.A.L test | <0.25 IU/ml | <0.25 IU/ml | <0.25 IU/ml | <0.25 IU/ml |
| | Microbial contamination | | | | |
| | Bacteria | ≦10 CFU/100 ml | 2 | 2 | 2 |
| | Funghi | ≦10 CFU/100 ml | 0 | 0 | 0 |
| Control of the solution | clarity and opalescence | ≦Standard I ≦Standard R7 and YB7 | ≦Standard I ≦Standard R7 and YB7 | ≦Standard I ≦Standard R7 and YB7 | ≦Standard I ≦Standard R7 and YB7 |
| | density | close to 1.0110 | 1.0069 | 1.0069 | 1.0069 |
| | microbial contamination of the solution before filtration | ≦10 CFU/ml | <10 | <10 | <10 |
| | microbial contamination between both filtrations | ≦10 CFU/100 ml | 0 | 0 | 0 |
| Filling | Distribution volume | ≧5.0 ml | 5.30 ml | 5.20 ml | 5.20 ml |
| | Dissolved O₂ | ≦3 ppm | 1.13 ppm | 1.16 ppm | 0.85 ppm | d) Controls on Finished Product

The controls have been carried out on 5 samples per batch taken all along the manufacturing process.

| Nature of controls | Specification | Beginning | ¼ | Middle | ¾ | End |
| --- | --- | --- | --- | --- | --- | --- |
| Batch F | | | | | | |
| Appearance | | | | | | |
| Clarity | Clear | Clear | Clear | Clear | Clear | Clear |
| Colour | ≦YB7 | YB7 | YB7 | YB7 | YB7 | YB7 |

-continued

| Nature of controls | Specification | Beginning | ¼ | Middle | ¾ | End |
|---|---|---|---|---|---|---|
| Impurities | | | | | | |
| 1) | ≦0.05 p. cent | <0.0002 | <0.0002 | <0.0002 | <0.0002 | <0.0002 |
| 2) | ≦0.05 p. cent | <0.0002 | <0.0002 | <0.0002 | <0.0002 | <0.0002 |
| Assay | 47.5 to 52.5 mg | 50.74 | 50.78 | 50.59 | 50.52 | 50.54 |
| | | | Batch G | | | |
| Appearance | | | | | | |
| Clarity | Clear | Clear | Clear | Clear | Clear | Clear |
| Colour | ≦YB7 | YB7 | YB7 | YB7 | YB7 | YB7 |
| Impurities | | | | | | |
| 1) | ≦0.05 p. cent | <0.0002 | <0.0002 | <0.0002 | <0.0002 | <0.0002 |
| 2) | ≦0.05 p. cent | <0.0002 | <0.0002 | <0.0002 | <0.0002 | <0.0002 |
| Assay | 47.5 to 52.5 mg | 50.64 | 50.13 | 50.27 | 50.16 | 49.86 |
| | | | Batch H | | | |
| Appearance | | | | | | |
| Clarity | Clear | Clear | Clear | Clear | Clear | Clear |
| Colour | ≦YB7 | YB7 | YB7 | YB7 | YB7 | YB7 |
| Impurities | | | | | | |
| 1) | ≦0.05 p. cent | <0.0002 | <0.0002 | <0.0002 | <0.0002 | <0.0002 |
| 2) | ≦0.05 p. cent | <0.0002 | <0.0002 | <0.0002 | <0.0002 | <0.0002 |
| Assay | 47.5 to 52.5 mg | 50.19 | 50.18 | 50.61 | 49.96 | 49.09 |

EXAMPLE 4

Adrenaline Hydrochloride Injection

When operating as in example 1, starting from 0.25 g of adrenaline hydrochloride, 1000 ampoules containing 0.25 mg of adrenaline each are obtained.

EXAMPLE 5

Isoprenaline Hydrochloride Injection

When operating as in example 1, starting from 2.00 g of isoprenaline hydrochloride, 10000 ampoules containing 0.2 mg of isoprenaline hydrochloride each are obtained.

EXAMPLE 6

Dopamine Hydrochloride Injection

Starting from 2.00 g of dopamine hydrochloride operating as in example 1, 10000 ampoules containing 0.2 mg of dopamine hydrochloride each are obtained.

EXAMPLE 7

Dobutamine Injection

When operating as in example 1 procedure, starting from 2500 g of dopamine hydrochloride, 10000 ampoules containing 250 mg of dobutamine each are obtained.

EXAMPLE 8

Dipivefrine Injection

When operating as in example 1 procedure, starting from 100 g of dipivefrine hydrochloride, 10000 ampoules containing 0.01 g of dipivefrine each are obtained.

EXAMPLE 9

Terbutaline Injection

When operating as in example 1 procedure, starting from 5000 g of terbutaline sulphate, 10000 ampoules containing 0.5 g of terbutaline (sulphate) each are obtained.

The invention claimed is:

1. A process to obtain stabilized phenolic substances solutions, antioxidant agent-free, comprising deoxygenating water and catecholamines solutions by an inert gas and gas holdups of the manufacturing tanks and pipes are deoxygenated before and after filling by a dense rare gas operating at 0–20 C. maintaining the pH in acid medium and then sterilizing the injectable solution by a double sterilizing filtration at room temperature.

2. The process of claim 1 wherein the active principle is dissolved in continuously deoxygenated water and placed in vials for injections.

3. The process of claim 1 wherein the oxygen content of water is lower than or equal to 0.02 ppm.

4. A process of claim 1 wherein the deoxyenation of gas holdups of tanks and pipes is carried out by bubbling of a dense rare gas.

5. The process of claim 1 wherein the water and solution temperature is maintained between 8° C. and 10° C.

6. The process of claim 1 wherein the acid pH of the solution during manufacture is adjusted to a value higher than 3.0.

7. The process of claim 1 wherein the pH of the solution during manufacture is adjusted to a value lower than 5.0.

8. The process of claim 1 wherein the sterilization is carried out by filtration through a filter having a 0.22 μm porosity.

9. The process of claim 1 wherein the inert gas is argon and the pressure for vials inerting is about 3 bars.

10. The process of claim 2 wherein the argon pressure for vials inerting is about 7.5 bars.

11. The process of claim 1 wherein the phenolic substance is noradrenaline at a dose of 0.2 mg/ml.

12. The process of claim 1 wherein the phenolic substance is adrenaline at a dose of 0.025 to 0.1%.

13. The process of claim 1 wherein the phenolic substance is dopamine hydrochloride at a dose of 50 and 200 mg.

14. The process of claim 1 wherein the phenolic substance is dobutamine sulfate at a dose of 250 mg.

* * * * *